United States Patent
Hamada et al.

(10) Patent No.: US 10,186,880 B2
(45) Date of Patent: Jan. 22, 2019

(54) MONITORING APPARATUS, MONITORING SYSTEM, MONITORING METHOD, AND NON-TRANSITORY STORAGE MEDIUM

(71) Applicant: NEC Corporation, Tokyo (JP)

(72) Inventors: Tatsushi Hamada, Tokyo (JP); Tsuyoshi Satou, Tokyo (JP); Takashi Kobayashi, Tokyo (JP); Togo Murakami, Tokyo (JP)

(73) Assignee: NEC Corporation, Tokyo (JP)

( * ) Notice: Subject to any disclaimer, the term of this patent is extended or adjusted under 35 U.S.C. 154(b) by 43 days.

(21) Appl. No.: 15/320,163

(22) PCT Filed: Jun. 18, 2015

(86) PCT No.: PCT/JP2015/067559
§ 371 (c)(1),
(2) Date: Dec. 19, 2016

(87) PCT Pub. No.: WO2015/194618
PCT Pub. Date: Dec. 23, 2015

(65) Prior Publication Data
US 2017/0126030 A1    May 4, 2017

(30) Foreign Application Priority Data

Jun. 20, 2014 (JP) ................ 2014-127428

(51) Int. Cl.
*H02J 7/00* (2006.01)
*G06Q 50/06* (2012.01)
(Continued)

(52) U.S. Cl.
CPC ....... *H02J 7/0021* (2013.01); *A61M 16/0003* (2014.02); *G01R 31/3606* (2013.01);
(Continued)

(58) Field of Classification Search
CPC .............. H02J 7/0021; A61M 16/0003; A61M 2205/8212
See application file for complete search history.

(56) References Cited

U.S. PATENT DOCUMENTS

| 6,147,601 A | 11/2000 | Sandelman et al. |
| 2008/0195414 A1* | 8/2008 | Duckert ............... A61B 5/0002 705/2 |

(Continued)

FOREIGN PATENT DOCUMENTS

| JP | 2004-15882 | 1/2004 |
| JP | 2004-246811 | 9/2004 |

(Continued)

OTHER PUBLICATIONS

International Search Report and Written Opinion dated Sep. 15, 2015, in corresponding PCT International Application.

*Primary Examiner* — Jermele M Hollington
*Assistant Examiner* — Alvaro Fortich
(74) *Attorney, Agent, or Firm* — Finnegan, Henderson, Farabow, Garrett & Dunner, L.L.P.

(57) ABSTRACT

Disclosed is a monitoring apparatus (10) including a user management unit (11) that acquires, in association with each of plural users, a residual power level of a storage battery used by the user, a detection unit (12) that detects a predetermined event, and a setting unit (13) that sets, when the predetermined event is detected, the degree of urgency of need for a predetermined measure for each user based on the residual power level of the storage battery.

14 Claims, 17 Drawing Sheets

(51) Int. Cl.
    *H02J 7/34*          (2006.01)
    *H02J 9/06*          (2006.01)
    *H02J 13/00*        (2006.01)
    *H04Q 9/00*        (2006.01)
    *A61M 16/00*       (2006.01)
    *G01R 31/36*       (2006.01)

(52) U.S. Cl.
    CPC ......... *G01R 31/3693* (2013.01); *G06Q 50/06* (2013.01); *H02J 7/00* (2013.01); *H02J 7/34* (2013.01); *H02J 9/06* (2013.01); *H02J 9/061* (2013.01); *H02J 13/00* (2013.01); *H04Q 9/00* (2013.01); *A61M 2205/8212* (2013.01)

(56) References Cited

U.S. PATENT DOCUMENTS

2010/0088120 A1\* 4/2010 Gonzalvo ............. G06Q 10/10
                                                               705/3

2010/0253289 A1\* 10/2010 Amir .................... H02J 7/0063
                                                            320/135
2010/0280847 A1\* 11/2010 Schaffer ................ G06F 19/345
                                                            705/3
2012/0239949 A1\* 9/2012 Kalyanasundaram ........................
                                                          G06F 1/3212
                                                            713/320
2014/0149332 A1   5/2014 Tanaka et al.
2014/0159918 A1\* 6/2014 Pichard .................... A61N 1/39
                                                          340/870.07

FOREIGN PATENT DOCUMENTS

| JP | 2007-510968 | 4/2007 |
| JP | 2009-130860 | 6/2009 |
| JP | 2013-97641 | 5/2013 |
| JP | 2013-143814 | 7/2013 |
| WO | WO 2013/002155 A1 | 1/2013 |

\* cited by examiner

FIG. 5

| MONITORING TARGET USER ID | STORAGE BATTERY ID |
|---|---|
| 0000001 | B 000001 |
| 0000002 | B 072135 |
| ⋮ | ⋮ |

FIG. 6

| STORAGE BATTERY ID | RESIDUAL LEVEL (kwh) |
|---|---|
| B 000001 | 2.50 |
| B 072135 | 0.82 |
| ⋮ | ⋮ |

FIG. 7

| MONITORING TARGET USER NAME | DEGREE OF URGENCY |
|---|---|
| ○○ ○○ | LOW |
| ×× ×× | HIGH |
| △△ △△ | LOW |
| ⋮ | ⋮ |

FIG. 10

| MONITORING TARGET USER NAME | PRIORITY RANK |
|---|---|
| ○○ ○○ | 15 |
| ×× ×× | 2 |
| △△ △△ | 13 |
| ⋮ | ⋮ |

FIG. 12

| STORAGE BATTERY ID | POWER CONSUMPTION PACE (w) |
|---|---|
| B 000001 | 515 |
| B 072135 | 498 |
| ⋮ | ⋮ |

FIG. 13

| STORAGE BATTERY ID | INSTALLATION POSITION |
|---|---|
| B 000001 | TOKYO ○○○○○ |
| B 072135 | OSAKA ××××× |
| ⋮ | ⋮ |

FIG. 14

| STORAGE BATTERY ID | INSTLLATION POSITION | DISTANCE TO REFERENCE POSITION (km) |
|---|---|---|
| B 000001 | TOKYO ○○○○○ | 1.5 |
| B 072135 | OSAKA × × × × × | 0.8 |
| ⋮ | ⋮ | ⋮ |

MONITORING APPARATUS, MONITORING SYSTEM, MONITORING METHOD, AND NON-TRANSITORY STORAGE MEDIUM

CROSS-REFERENCE TO RELATED PATENT APPLICATIONS

This application is a National Stage Entry of International Application No. PCT/JP2015/067559, filed Jun. 18, 2015, which claims priority from Japanese Patent Application No. 2014-127428, filed Jun. 20, 2014. The entire contents of the above-referenced applications are expressly incorporated herein by reference.

TECHNICAL FIELD

The present invention relates to a monitoring apparatus, a monitoring system, a monitoring method, and a program.

BACKGROUND ART

There are users for whom it is necessary to continuously operate a predetermined electrical device. For example, a user who undergoes home treatment using a medical device such as a ventilator or an artificial dialyzer corresponds to such a user.

For such a user, it is necessary to provide a method for avoiding inconvenience that an electrical device is unintentionally stopped due to cutoff of power supply from a system due to a power failure or the like. For example, by employing a configuration in which a storage battery is provided and power is supplied from the storage battery to the electrical device when power supply from a system is cut off, it is possible to reduce such inconvenience. However, power that can be supplied from the storage battery is limited. Thus, when power supply from a system is stopped, it is necessary to perform a certain measure such as charging the storage battery or rescuing (transferring the user to a place where a private power generation facility is provided).

Related techniques are disclosed in Patent Documents 1 to 3.

Patent Document 1 discloses a technique that can make reference to necessary medical information in a case where telecommunication is not possible at a home visit or in a case where there are plural home visits. Specifically, the disclosed technique relates to a medical division system in which a server that includes a medical information storage unit that stores medical information for each patient transmit and receive the medical information to and from a terminal through a network. At least one of the server or the terminal includes a specification unit that specifies a timing when the terminal acquires the medical information based on home visit information in which sets of positional information indicating a location of a home visit, telecommunication information indicating whether the location of a home visit has a telecommunicable environment, and patient identification information associated with each other are arranged in the order of home visits.

Patent Document 2 discloses a portable terminal capable of extending a usable time of a function having reached a residual power level corresponding to an amount of a time set by a user, and assigning priority ranks to three or more functions to ensure the respective functions in the priority order. Specifically, Patent Document 2 discloses a portable terminal that includes a function for executing plural applications. The portable terminal includes a battery that performs power supply, a residual power level measurement unit that measures a residual power level of the battery, a storage unit, a comparison unit, and a control unit. The storage unit stores a priority rank of each application, and a reference value of the residual power level corresponding to a guaranteed operation time set for each application. The comparison unit compares a residual power level measured by the residual power level measurement unit with the reference value of the residual power level stored in the storage unit. The control unit specifies, when it is detected by the comparison unit that the measured residual power level is equal to or lower than the reference value of the residual power level, an application of which a priority rank is set to be lower than a priority rank stored corresponding to the reference value of the residual power level, and stops an operation of the specified application.

Patent Document 3 discloses a remote control server that can perform a remote control based on a portable terminal. Specifically, Patent Document 3 discloses a remote control server that performs a remote control of a portable terminal at each of predetermined timings. The server includes a transmission unit, a reception unit, and a control unit. The transmission unit transmits trigger information for starting a remote control of the portable terminal to the portable terminal at each of predetermined timings. The reception unit receives state information of the portable terminal transmitted from the portable terminal in response to the trigger information. The control unit performs a remote control of the portable terminal based on the state information received by the reception unit.

RELATED DOCUMENTS

Patent Documents

[Patent Document 1] Japanese Unexamined Patent Application Publication No. 2013-97641
[Patent Document 2] Japanese Unexamined Patent Application Publication No. 2009-130860
[Patent Document 3] Japanese Unexamined Patent Application Publication No. 2004-246811

SUMMARY OF THE INVENTION

Technical Problem

As described above, even when a user who wants to continuously operate a predetermined electrical device prepares against a power failure or the like using a storage battery, since power that can be supplied from the storage battery is limited, when power supply from a system is cut off, it is necessary to perform a certain measure such as charging the storage battery or rescuing (transfer to a place where a home power generation facility is provided). In a case where there are plural users who are targets for the measures, it is necessary to determine priority ranks of measures. However, there are no techniques for assisting determination of the priority ranks.

An object of the invention is to provide a technique for assisting, when a predetermined event (for example, a power failure) occurs, determination of priority ranks of predetermined measures (for example, charging a storage battery, exchange of a storage battery, other measures for operating an electrical device normally, or rescues) with respect to plural users who need the measures.

Solution to Problem

According to an aspect of the invention, there is provided a monitoring apparatus including: a user management unit that acquires, in association with each of plural users, a residual power level of a storage battery used by each user; a detection unit that detects a predetermined event; and a setting unit that sets, when the predetermined event is detected, the degree of urgency of need for a predetermined measure for each user based on the residual power level of the storage battery.

According to another aspect of the invention, there is provided a program that causes a computer to function as: a user management unit that acquires, in association with each of plural users, a residual power level of a storage battery used by each user; a detection unit that detects a predetermined event; and a setting unit that sets, when the predetermined event is detected, the degree of urgency of need for a predetermined measure for each user based on the residual power level of the storage battery.

According to still another aspect of the invention, there is provided a monitoring method executed by a computer, the method including: a user management step of acquiring, in association with each of plural users, a residual power level of a storage battery used by each user; a detection step of detecting a predetermined event; and a setting step of setting, when the predetermined event is detected, the degree of urgency of need for a predetermined measure for each user based on the residual power level of the storage battery.

According to still another aspect of the invention, there is provided a monitoring system including: a monitoring apparatus that includes a user management unit that acquires, in association with each of plural users, a residual power level of a storage battery used by each user, a detection unit that detects a predetermined event, and a setting unit that sets, when the predetermined event is detected, the degree of urgency of need for a predetermined measure for each user based on the residual power level of the storage battery; and the storage battery that notifies the monitoring apparatus of the residual power level.

Advantageous Effects of Invention

According to the invention, it is possible to realize a technique for assisting, when a predetermined event (for example, a power failure) occurs, determination of priority ranks of predetermined measures (for example, charging of a storage battery, exchange of a storage battery, other measures for operating an electrical device normally, or rescues) with respect to plural users who need the measures.

BRIEF DESCRIPTION OF THE DRAWINGS

The above object, other objects, features and advantages will become apparent from preferred exemplary embodiments to be described below and the accompanying drawings.

FIG. 5 is a diagram schematically showing an example of information managed by a monitoring apparatus of an exemplary embodiment.

FIG. 6 is a diagram schematically showing an example of information managed by a user management unit 11 of an exemplary embodiment.

FIG. 7 is a diagram schematically showing an example of information output by a first output unit 14 of an exemplary embodiment.

FIG. 10 is a diagram schematically showing an example of information output by a second output unit 16 of an exemplary embodiment.

FIG. 12 is a diagram schematically showing an example of information managed by the user management unit 11 of an exemplary embodiment.

FIG. 13 is a diagram schematically showing an example of information managed by the user management unit 11 of an exemplary embodiment.

FIG. 14 is a diagram schematically showing an example of information managed by the user management unit 11 of an exemplary embodiment.

DESCRIPTION OF EXEMPLARY EMBODIMENTS

First, an example of a hardware configuration of an apparatus of an exemplary embodiment will be described. Respective components provided in the apparatus of the exemplary embodiment are configured by an arbitrary combination of hardware and software including a central processing unit (CPU), a memory, a program loaded in the memory (including a program stored in a memory in a stage where an apparatus is delivered in advance, or a program downloaded from a storage medium such as a compact disc (CD), a server on the Internet, or the like), a storage unit such as a hard disk that stores the program, and a network connection interface in an arbitrary computer. Further, it can be understood by those skilled in the art that various modifications may be performed with respect to a configuration method and an apparatus thereof.

Figure 1:
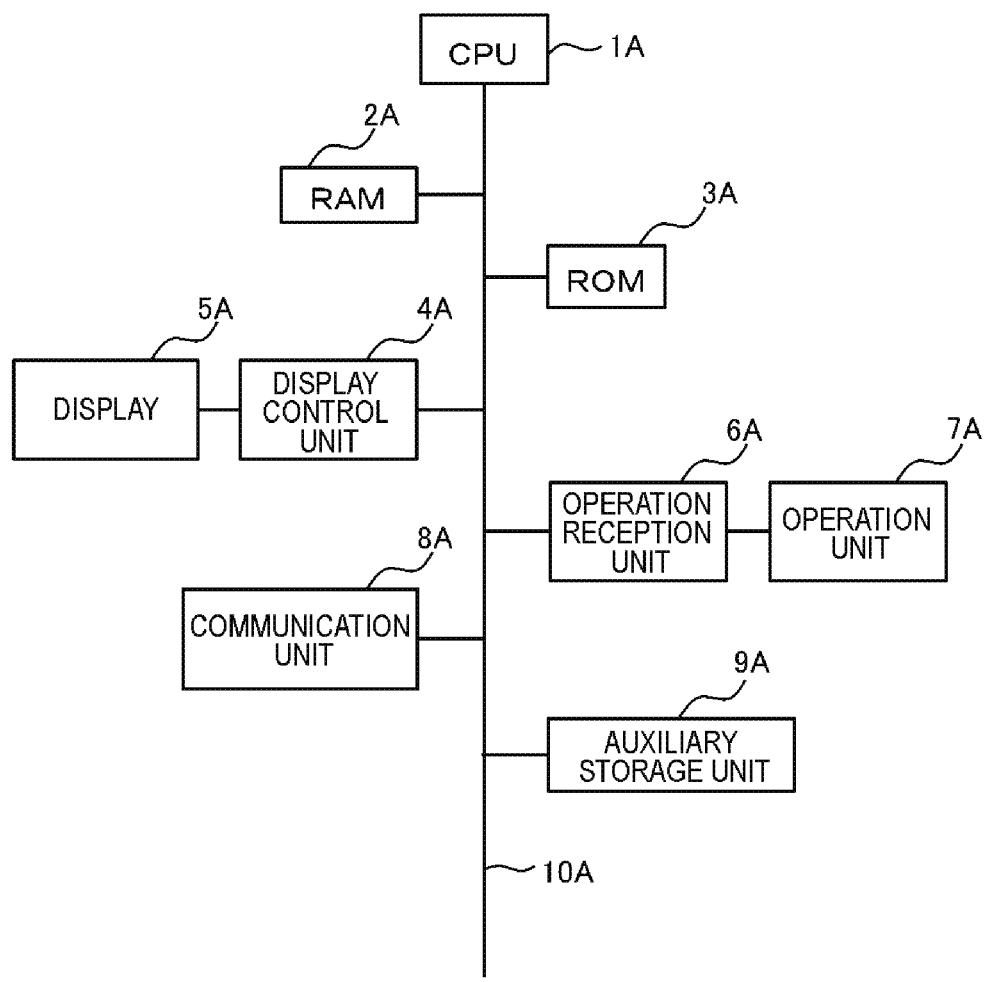
FIG. 1 is a diagram conceptually showing an example of a hardware configuration of an apparatus of an exemplary embodiment.

FIG. 1 is a diagram conceptually showing an example of a hardware configuration of an apparatus of an exemplary embodiment. As shown, the apparatus of the exemplary embodiment includes a CPU 1A, a random access memory (RAM) 2A, a read only memory (ROM) 3A, a display control unit 4A, a display 5A, an operation reception unit 6A, an operation unit 7A, a communication unit 8A, and an auxiliary storage unit 9A, for example, which are connected to each other through a bus 10A. Although not shown, the apparatus may include other components such as an input/output interface which is connected to an external device in a wired manner, a microphone, or a speaker.

The CPU 1A controls the entirety of a computer of the apparatus together with the respective components. The ROM 3A includes areas in which a program for operating the computer, various application programs, a variety of setting data to be used when the programs are operated, and the like are stored. The RAM 2A includes an area in which data is temporarily stored, such as a work area for operating a program. The auxiliary storage unit 9A is a hard disk drive (HDD), for example, which may store a large amount of data.

The display 5A is a display device (a light emitting diode (LED) display, a liquid crystal display, an organic electro luminescence (EL) display, or the like), for example. The display 5A may be a touch panel display which is integrated with a touch pad. The display control unit 4A reads data stored in a video RAM (VRAM) and performs a predetermined process with respect to the read data, and then, transmits the result to the display 5A to perform various screen displays. The operation reception unit 6A receives various operations through the operation unit 7A. The operation unit 7A includes operation keys, operation buttons, a switch, a jog dial, a touch panel display, a keyboard, or the like. The communication unit 8A is connected to a network such as the Internet or a local area network (LAN) in a wired and/or wireless manner, and communicates with other electrical devices.

Hereinafter, the exemplary embodiment will be described. Functional block diagrams used in description of the following exemplary embodiments show blocks in units of functions instead of configurations in units of hardware. In the following figures, an example in which each apparatus is configured by one device is shown, but its configuration method is not limited thereto. That is, physically divided configurations or logically divided configurations may be used. The same reference numerals are given to the same components, and description thereof will not be repeated as necessary.

First Exemplary Embodiment

Figure 2:
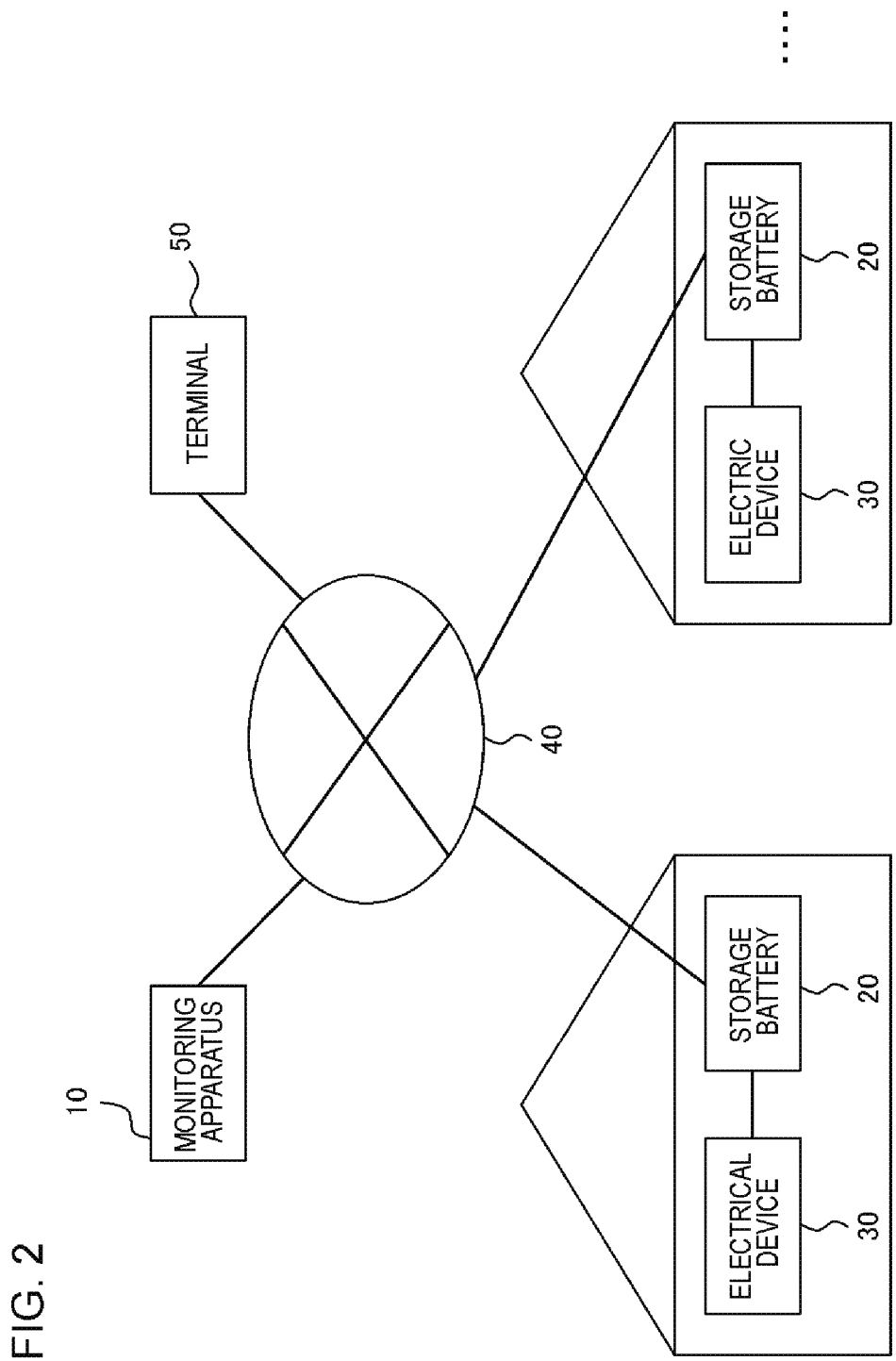
FIG. 2 is a diagram showing an example of functional blocks of a monitoring system of an exemplary embodiment.

First, an outline of this exemplary embodiment will be described. FIG. 2 is a functional block diagram showing a monitoring system of this exemplary embodiment in perspective. The monitoring system of this exemplary embodiment includes a monitoring apparatus 10 and plural storage batteries 20.

The storage battery 20 is connected to an electrical device 30, and supplies power to the electrical device 30. The storage battery 20 may employ all configurations such as a lead storage battery or a lithium ion secondary battery. The storage battery 20 has a function for measuring a residual power level in the storage battery. Further, the storage battery 20 has a function for connecting to a network 40 such as the Internet. The storage battery 20 having such functions may be realized based on known techniques.

The electrical device 30 is an electrical device that needs to be continuously operated. The type of the electrical device 30 is not particularly limited, and for example, may be a medical device such as a ventilator or an artificial dialyzer.

The monitoring apparatus 10 assists determination of priority ranks of predetermined measures (for example, charging the storage battery 20, exchange of the storage battery 20, other measures for operating the electrical device 30 normally, or rescues) with respect to plural users based on information acquired from the storage battery 20 (for example, a residual power level of the storage battery) when a predetermined event (for example, a power failure) occurs.

For example, the monitoring apparatus 10 generates information indicating a material for determining a priority rank (for example, the degree of urgency of need for a predetermined measure), or directly determines the priority rank. An entity that executes the predetermined measures or a user who needs a predetermined process browses the information using a predetermined terminal 50. The entity includes, for example, a power supplier, a hospital, an organization that performs a rescue in an emergency, or the like. After browsing the information, the entity performs a process of determining the priority ranks of the predetermined measures with respect to the plural users based on the information, or the like, and then executes the predetermined measures according to the determined priority ranks.

The monitoring apparatus 10, the storage battery 20, and the terminal 50 are connected to each other through the network 40. For example, these components may be connected to each other through a communication infra (network 40) that includes a backup power source facility and is operable even in the case of cutoff of power supply from a system such as a power failure. With this configuration, even during the power failure, the monitoring apparatus 10 may acquire the latest information from the storage battery 20 through the network 40, and may assist determination of the priority ranks of the predetermined measures with respect to the plural users based on the latest information. Further, the monitoring apparatus 10 may transmit the generated predetermined information to the terminal 50 through the network 40.

The storage battery 20 provided in each household may be configured so that the storage battery 20 is not connected to the network 40 during a power failure (for example, so that a LAN where the storage battery 20 is present stops its operation during a power failure). Even in such a case, the monitoring apparatus 10 may assist determination of the priority ranks of the predetermined measures with respect to the plural users based on the information acquired from the storage battery 20 immediately before the power failure. Further, the monitoring apparatus 10 may transmit the generated predetermined information to the terminal 50 through the network 40.

Figure 3:
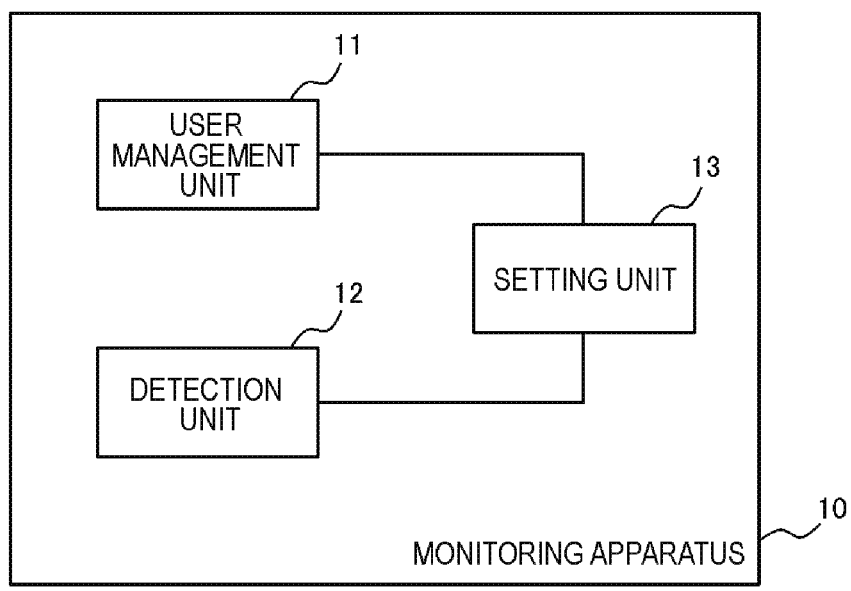
FIG. 3 is a diagram showing an example of functional blocks of a monitoring apparatus of an exemplary embodiment.
Figure 4:
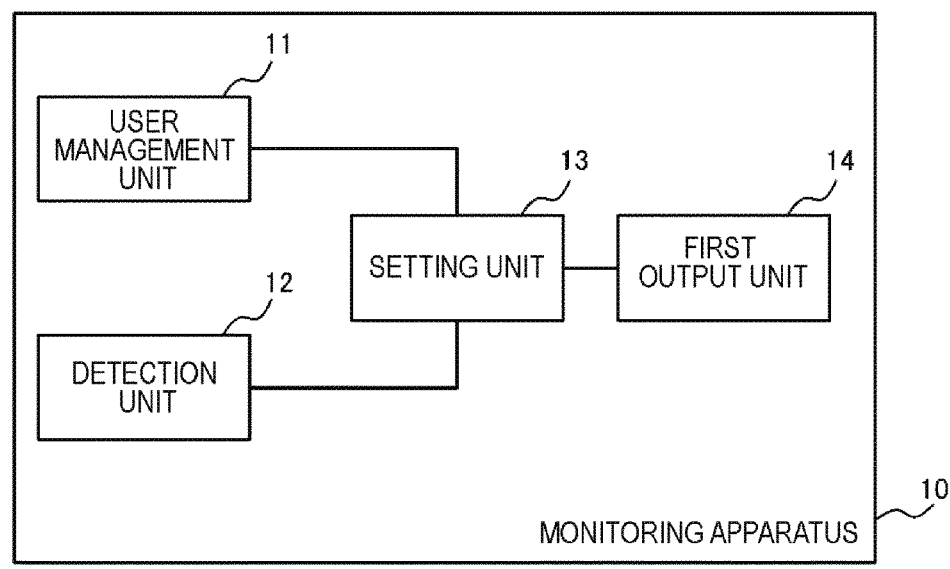
FIG. 4 is a diagram showing an example of functional blocks of a monitoring apparatus of an exemplary embodiment.

Next, the configuration of the exemplary embodiment will be described in detail. FIG. 3 shows an example of functional blocks of the monitoring apparatus 10 of the exemplary embodiment. The monitoring apparatus 10 shown in FIG. 3 includes a user management unit 11, a detection unit 12, and a setting unit 13. FIG. 4 shows another example of the functional blocks of the monitoring apparatus 10 of this exemplary embodiment. The monitoring apparatus 10 shown in FIG. 4 is different from the monitoring apparatus 10 shown in FIG. 3 in that a first output unit 14 is provided. Hereinafter, respective components will be described.

The user management unit 11 acquires and manages, in association with each of plural monitoring target users, a residual power level of the storage battery 20 which is used by each of the monitoring target users.

A user (hereinafter, referred to as a "monitoring target user") who needs a continuous operation of a predetermined electrical device (for example, a medical device) and needs a predetermined measure (for example, charging the storage battery 20, exchange of the storage battery 20, other measures for operating the electrical device 30 normally, or rescues) when a predetermined event (for example, a power failure) occurs is registered in advance in the monitoring apparatus 10. Further, identification information of the storage battery 20 used by the monitoring target user as a backup power source of the electrical device is registered in the monitoring apparatus 10. FIG. 5 schematically shows an example of registered information. In the registered information shown in FIG. 5, identification information for the monitoring target user (monitoring target user ID) and identification information for the storage battery (storage battery ID) are associated with each other. In addition, information for communication of the monitoring apparatus 10 with the storage battery 20 (address information of the storage battery 20, or the like) or individual information for the monitoring target user (name, gender, age, address, or the like) may be registered in the monitoring apparatus 10.

The user management unit 11 acquires, at a predetermined timing, information indicating a residual power level at that point in time from the storage battery 20 registered in the monitoring apparatus 10. Further, the user management unit 11 manages the residual power level of the storage battery 20 used by each of the monitoring target users based on the information. FIG. 6 schematically shows an example of information managed by the user management unit 11. The information shown in FIG. 6 is updated based on the latest information (the residual power level of each storage battery 20) acquired by the user management unit 11.

As the timing when the user management unit 11 acquires the information indicating the residual power level from the storage battery 20, a timing of a predetermined time interval (for example, every minute, every 5 minutes, every 15 minutes, or every 30 minutes) may be considered. For example, at such a predetermined time interval, the storage battery 20 may spontaneously transmit information indicating a residual power level at that point in time to the monitoring apparatus 10. Alternatively, the monitoring apparatus 10 may request information indicating a residual power level from the storage battery 20 at the predetermined time interval. Further, the storage battery 20 may transmit, in response to the request, the information indicating the residual power level at that point in time to the monitoring apparatus 10.

In a case where the monitoring apparatus 10 and the storage battery 20 are configured to communicate with each other even after a predetermined event occurs, the user management unit 11 may request the information from the storage battery 20 in response to detection of the predetermined event, without acquiring information indicating a residual power level from the storage battery 20 before the predetermined event is detected. Further, the storage battery 20 may transmit, in response to the request, the information indicating the residual power level at that point in time to the monitoring apparatus 10. Alternatively, the storage battery 20 may transmit, in response to the detection of the predetermined event, the information indicating the residual power level at that point in time to the monitoring apparatus 10.

The detection unit 12 detects a predetermined event. For example, the predetermined event is cutoff of power supply from a system (power failure), for example. The detection unit 12 receives an input of information indicating the occurrence of the event. Further, the detection unit 12 detects the occurrence of the predetermined event based on the input.

The input of the information indicating the occurrence of the event may be performed by an operator who operates the monitoring apparatus 10, for example. For example, if the occurrence of the event is detected based on the news through a medium such as a television, a radio, or the Internet, or based on a notification from a power supplier using an arbitrary method, the operator who operates the monitoring apparatus 10 may input information indicating the occurrence of the event to the monitoring apparatus 10.

Alternatively, the information indicating the occurrence of the event may be input to the monitoring apparatus 10 through the network 40 from an apparatus used by an organization that manages power supply (for example, a power supplier, a person who manages power supply, or the like). Further, the detection unit 12 may receive the input. For example, if the occurrence of the event is detected, an organization that manages power supply (for example, a power supplier, a person who manages power supply, or the like) inputs information indicating the detection of the occurrence of the event to a predetermined apparatus. Alternatively, the predetermined apparatus may continuously monitor a power supply network to automatically detect the occurrence of the event. Further, the apparatus that has received the input of the information indicating the occurrence of the event transmits information indicating the reception to the monitoring apparatus 10 through the network 40.

In addition, in a case where the monitoring apparatus 10 and the storage battery 20 are configured to communicate with each other even after a predetermined event occurs, the monitoring apparatus 10 may acquire information indicating the occurrence of the predetermined event from the storage battery 20. Further, the detection unit 12 may receive an input of the information. In this case, the storage battery 20 is continuously connected to the system, and determines, if power supply from the system is cut off, that the predetermined event (for example, a power failure) occurs. Further, the storage battery 20 transmits the information indicating the occurrence of the predetermined event to the monitoring apparatus 10.

If a predetermined event is detected by the detection unit 12, the setting unit 13 sets the degree of urgency of need for a predetermined measure for each monitoring target user based on a residual power level of the storage battery 20 managed by the user management unit 11. For example, the setting unit 13 sets the degree of urgency higher as the residual power level of the storage battery 20 is lower.

The setting unit 13 retains information (a function, a table, or the like) for setting the degree of urgency based on the residual power level. Details about the information are not particularly limited, but for easy understanding of the information, an example is shown as follows. For example, the information may be information such that "degree of urgency: low" is set in a case where the residual level is equal to or greater than 4 kWh, "degree of urgency: intermediate" is set in a case where the residual level is equal to or greater than 1 kWh and is smaller than 4 kWh, "degree of urgency: high" is set in a case where the residual level is equal to or greater than 0.5 kWh and is smaller than 1 kWh, and "degree of urgency: extra-high" is set in a case where the residual level is smaller than 0.5 kWh.

A residual level of a storage battery may increase, or a reduction pace thereof may become moderate according to a spontaneous behavior of each monitoring target user. Further, the inconvenience that the residual level of the storage battery 20 rapidly decreases due to an unexpected situation is considered. Thus, in a case where the monitoring apparatus 10 and the storage battery 20 are configured to communicate with each other even after a predetermined event occurs, the user management unit 11 may acquire and update the residual power level of the storage battery 20 at a predetermined timing even after the predetermined event occurs. Further, the setting unit 13 may update the degree of urgency based on the latest information.

The first output unit 14 outputs the degree of urgency set by the setting unit 13. In a case where the degree of urgency is updated, the first output unit 14 outputs the latest degree of urgency whenever the degree of urgency is updated. An output method is not particularly limited. For example, an output may be performed through the display 5A provided in the monitoring apparatus 10, or may be performed through a printer connected to the communication unit 8A provided in the monitoring apparatus 10. Alternatively, the first output unit 14 may perform an output (transmission) toward the terminal 50 (see FIG. 2) through the communication unit 8A provided in the monitoring apparatus 10. For example, a mail address of an entity that performs a predetermined measure or a monitoring target user may be registered in advance, and the first output unit 14 may transmit the degree of urgency to a destination of the mail address. In addition, the first output unit 14 may register the degrees of urgency set by the setting unit 13 in a web server to open the degree of urgency on a network such as the Internet. Further, a predetermined user may access the web server using the terminal 50 to acquire or display the information.

FIG. 7 schematically shows an example of information output by the first output unit 14 toward an entity that performs a predetermined measure. The information shown in the figure indicates the degrees of urgency in association with names of monitoring target users. It is preferable that information for each monitoring target user is only the degree of urgency of each monitoring target user, instead of a list of the degrees of urgency of plural monitoring target users.

The setting unit 13 may further calculate the number of monitoring target users who belong to each of the degrees of urgency divided into plural levels or a ratio thereof. Further, the first output unit 14 may output the calculation result.

A monitoring target user who browses such information can recognize that he or she is understood as a predetermined measure target, and can know how his or her state (the degree of urgency) is recognized. Further, the monitoring target user can understand his or her state, or the like among the plural monitoring target users. As a result, it is possible to reduce his or her anxiety until the time of a measure.

Figure 8:
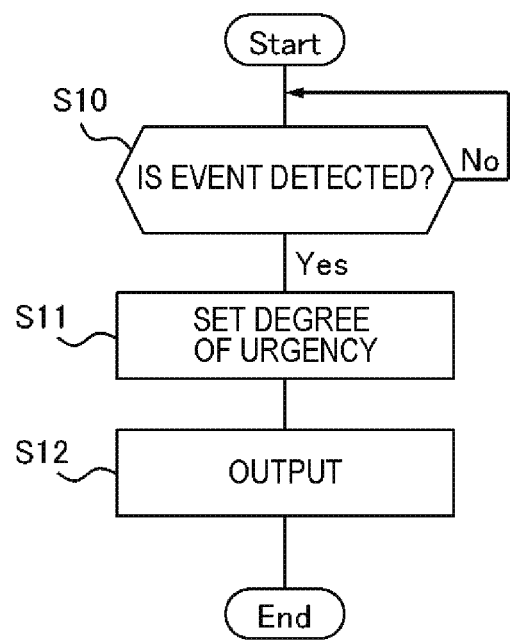
FIG. 8 is a flowchart showing an example of a processing flow of a monitoring apparatus of an exemplary embodiment.

Then, an example of a processing flow of the monitoring apparatus 10 of this exemplary embodiment will be described using a flowchart of FIG. 8.

The detection unit 12 monitors whether a predetermined event occurs (S10). The detection unit 12 continues monitoring until the predetermined event occurs (No in S10).

If the detection unit 12 detects the predetermined event (Yes in S10), the setting unit 13 sets the degree of urgency of need for a predetermined measure for each monitoring target user based on a residual power level of the storage battery 20 managed by the user management unit 11 (S11).

For example, at predetermined time intervals, the user management unit 11 repeatedly acquires information indicating a residual power level at that point in time from the storage battery 20 and manages a latest state (residual power level) of each storage battery 20 based on the information. Alternatively, if the predetermined event is detected in S10, the user management unit 11 acquires, in response thereto, information indicating a residual power level at that point in time from the storage battery 20, and manages a latest state (residual power level) of each storage battery 20 based on the information.

Then, the first output unit 14 outputs the degrees of urgency set in S11 (S12).

According to the above-described exemplary embodiment, when a predetermined event (for example, a power failure) occurs, it is possible to set the degree of urgency of need for a predetermined measures (for example, charging a storage battery, exchange of the storage battery, other measures for operating an electrical device 30 normally, or rescues) for each monitoring target user based on a residual power level of a storage battery at that point in time. Thus, it is possible to determine priority ranks of measures with respect to plural monitoring target users based on the degrees of urgency.

Second Exemplary Embodiment

A monitoring apparatus 10 of this exemplary embodiment is different from the first exemplary embodiment in that a function for determining priority ranks of predetermined measures (for example, charging a storage battery, or rescues) with respect to plural monitoring target users based on the degrees of urgency set by the setting unit 13 is provided.

Figure 9:
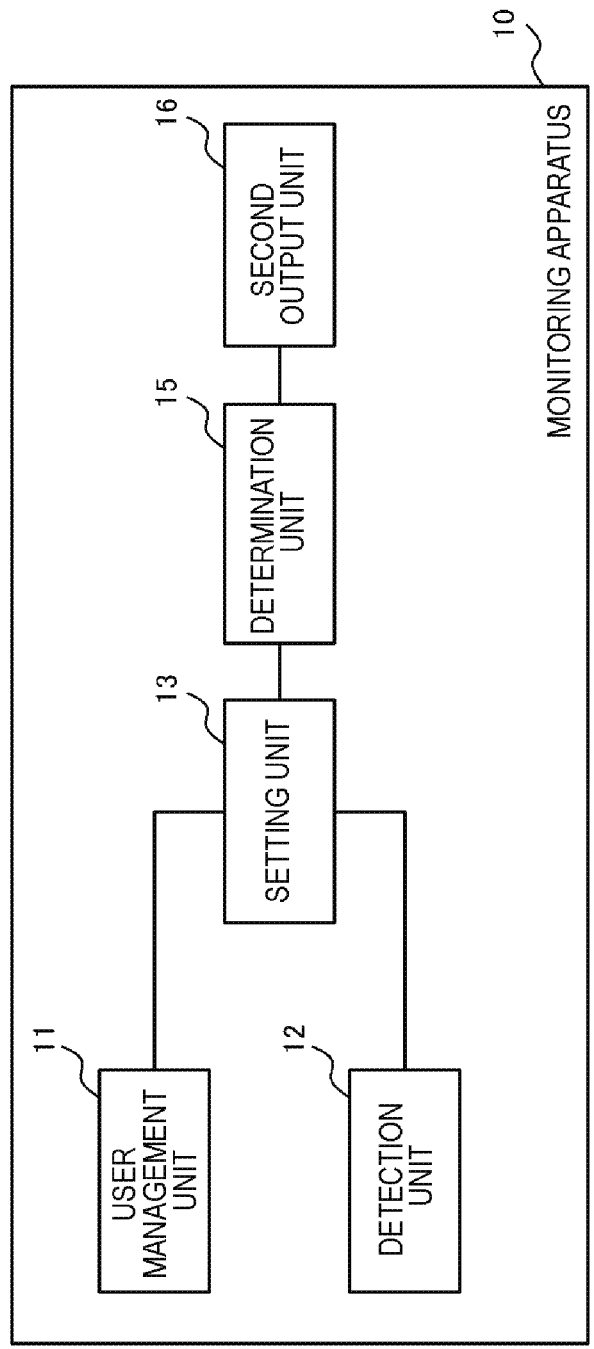
FIG. 9 is a diagram showing an example of functional blocks of a monitoring apparatus of an exemplary embodiment.

FIG. 9 shows an example of functional blocks of a monitoring apparatus 10 of this exemplary embodiment. As shown in the figure, the monitoring apparatus 10 of this exemplary embodiment includes a user management unit 11, a detection unit 12, a setting unit 13, a determination unit 15, and a second output unit 16. The monitoring apparatus 10 may further include a first output unit 14. Since configurations of the user management unit 11, the detection unit 12, the setting unit 13, and the first output unit 14 are the same as those of the first exemplary embodiment, description thereof will not be repeated. Hereinafter, the determination unit 15 and the second output unit 16 will be described.

The determination unit 15 determines priority ranks for performing predetermined measures with respect to plural monitoring target users based on the degrees of urgency set by the setting unit 13. For example, the determination unit 15 may set priority ranks of measures being preferentially performed in a descending order of the degrees of urgency. Hereinafter, a priority rank where a measure is preferentially performed is referred to as a high-priority rank. In a case where the degrees of urgency are at the same level, the determination unit 15 may determine priority ranks based on ages, genders, or the like of monitoring target users. For example, a high-priority rank may be given to children (for example, 13 years old or less), old persons (for example, 80 years old or more), women, or the like having a weak physical strength.

A residual level of a storage battery may increase, or a reduction pace thereof may become moderate according to a spontaneous behavior of each monitoring target user. Further, the residual level of the storage battery 20 may rapidly decrease due to an unexpected situation. Thus, in a case where the monitoring apparatus 10 and the storage battery 20 are configured to communicate with each other even after a predetermined event occurs, the user management unit 11 may acquire and update the residual power level of the storage battery 20 at a predetermined timing even after the predetermined event occurs. Further, the setting unit 13 may update the degree of urgency based on the latest information. In addition, the determination unit 15 may determine again and update the priority rank based on the latest degree of urgency.

The second output unit 16 outputs the priority rank determined by the determination unit 15. In a case where the priority rank is updated, the second output unit 16 outputs a latest priority rank every time. An output method is not particularly limited. For example, an output may be performed through a display 5A provided in the monitoring apparatus 10, or may be performed through a printer connected to the communication unit 8A provided in the monitoring apparatus 10. Alternatively, the second output unit 16 may perform an output (transmission) toward a terminal 50 (see FIG. 2) through the communication unit 8A provided in the monitoring apparatus 10. For example, a mail address of an entity that performs a predetermined measure or a monitoring target user may be registered in advance, and the second output unit 16 may transmit a priority rank to a destination of the mail address. Further, the second output unit 16 may register the priority rank determined by the determination unit 15 in a web server to open the determined priority rank on a network such as the Internet. Furthermore, a predetermined user may access the web server using the terminal 50 to acquire or display the information.

FIG. 10 schematically shows an example of information output by the second output unit 16 toward an entity that performs a predetermined measure. The information shown in the figure indicates priority ranks in association with names of monitoring target users. It is preferable that information for each monitoring target user is only a priority rank for each monitoring target user, instead of a list of priority rank of plural monitoring target users.

A monitoring target user who browses such information can recognize that he or she is understood as a predetermined measure target, and can know his or her priority rank, that is, the position of the monitoring target user on the measure waiting list. As a result, it is possible to reduce his or her anxiety until the time of a measure.

Figure 11:
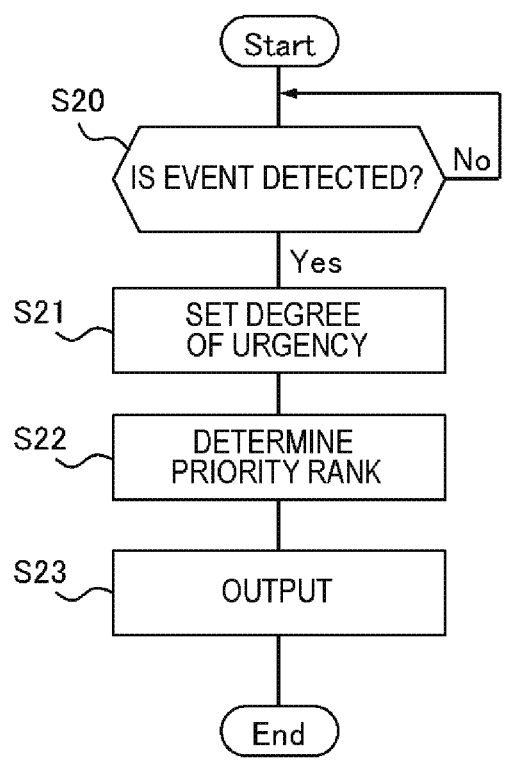
FIG. 11 is a flowchart showing an example of a processing flow of a monitoring apparatus of an exemplary embodiment.

Then, an example of a processing flow of the monitoring apparatus 10 of this exemplary embodiment will be described using a flowchart of FIG. 11.

The detection unit 12 monitors whether a predetermined event occurs (S20). The detection unit 12 continuously monitors until the predetermined event occurs (No in S20).

If the detection unit 12 detects the predetermined event (Yes in S20), the setting unit 13 sets the degree of urgency of need for a predetermined measure for each monitoring target user based on a residual power level of the storage battery 20 managed by the user management unit 11 (S21).

For example, at predetermined time intervals, the user management unit 11 repeatedly acquires information indicating a residual power level at that point in time from the storage battery 20 and manages a latest state (residual power level) of each storage battery 20 based on the information. Alternatively, if the predetermined event is detected in S20, the user management unit 11 acquires, in response thereto, information indicating a residual power level at that point in time from the storage battery 20, and manages a latest state (residual power level) of each storage battery 20 based on the information.

Then, the determination unit 15 determines priority ranks of performing predetermined measures with respect to plural monitoring target users based on the degree of urgency for each user set in S21 (S22). Thereafter, the second output unit 16 outputs the priority ranks determined in S22 (S23).

According to the above-described exemplary embodiment, when a predetermined event (for example, a power failure) occurs, it is possible to set the degree of urgency of need for a predetermined measure (for example, charging a storage battery, exchange of the storage battery, other measures or rescues for operating the electrical device 30 normally) with respect to each monitoring target user based on a residual power level of a storage battery at that point in time. Further, it is possible to determine priority ranks of measures with respect to plural monitoring target users based on the degrees of urgency, or the like. As a result, it is possible to execute predetermined measures with respect to plural monitoring target users based on the priority ranks in an appropriate order. Further, since the monitoring apparatus 10 determines the priority ranks, it is not necessary that an operator of a predetermined measure collects information for determining priority ranks or determines the priority ranks. Thus, the operator of the predetermined measure can rapidly start the predetermined measure.

Third Exemplary Embodiment

A monitoring apparatus 10 of this exemplary embodiment is different from the first and second exemplary embodiments in that a usage state of the storage battery 20 is further managed, and the degree of urgency is set in consideration of the usage state.

Functional blocks of the monitoring apparatus 10 of this exemplary embodiment are the same as in the first and second exemplary embodiments. Since configurations of the detection unit 12, the first output unit 14, the determination unit 15, and the second output unit 16 are the same as those of the first and second exemplary embodiments, description thereof will not be repeated. Hereinafter, configurations of a user management unit 11 and a setting unit 13 will be described.

The third exemplary embodiment is different from the first and second exemplary embodiments in that the user management unit 11 acquires and manages information indicating a usage state of each storage battery 20 in addition to a residual power level of the storage battery 20. The user management unit 11 manages a power consumption pace as a usage state, for example. FIG. 12 schematically shows an example of information managed by the user management unit 11. Storage battery IDs and power consumption paces are associated with each other in the information.

The power consumption pace is calculated by an expression of $(L2-L1)/(t2-t1)$ based on a residual power level ($L1$ (kWh)) of the storage battery 20 measured at a first timing ($t1$) and a residual power level ($L2$ (kWh)) of the storage battery 20 measured at a second timing ($t2$), for example. Plural pairs of the first timing and the second timing may be used to set a statistic value (average value, intermediate value, maximum value, minimum value, mode value, or the like) of values calculated using the above-mentioned expression for each pair as the power consumption pace. By setting the unit of ($t2-t1$) to time (hour), as shown in FIG. 12, the unit of power consumption pace may be set to Watts (W). However, determining the unit of the power consumption pace managed by the user management unit 11 is a matter of design.

It is preferable that the first timing ($t1$) and the second timing ($t2$) are close to a timing when the detection unit 12 detects an event. Thereby, it is possible to calculate a power consumption pace accurately indicating a current usage state. For example, the second timing ($t2$) may be a timing when the storage battery 20 measures a residual level immediately before a timing when the detection unit 12 detects the event, and the first timing ($t1$) may be a timing when the storage battery 20 measures a residual level immediately before the second timing.

Further, in a case where the monitoring apparatus 10 and the storage battery 20 are configured to communicate with each other even after a predetermined event occurs, the first timing ($t1$) and the second timing ($t2$) may be a timing after the timing when the detection unit 12 detects the event. Thereby, it is possible to accurately calculate a power consumption pace indicating a true usage state when the predetermined event occurs.

Further, there may be a user who does not normally use the storage battery 20 while causing power being supplied to the electrical device 30 from a system and supplies power to the electrical device 30 from the storage battery 20 only in an emergency when a predetermined event occurs. In the case of such a user, since the user does not use the storage battery 20 before the predetermined event occurs, if the first timing (t1) and the second timing (t2) are set to be prior to the timing when the detection unit 12 detects the event, a calculated power consumption pace becomes 0. Thus, by setting both of the first timing (t1) and the second timing (t2) to be later than the timing when the detection unit 12 detects the event, it is possible to avoid such an inconvenience.

The calculation of the power consumption pace may be performed by the monitoring apparatus 10, or may be performed by the storage battery 20. The user management unit 11 acquires the power consumption pace calculated by the monitoring apparatus 10 or the storage battery 20 for management.

The third exemplary embodiment is different from the first and second exemplary embodiments in that the setting unit 13 sets the degree of urgency based on the usage state (see FIG. 12) in addition to the residual power level (see FIG. 6) of the storage battery 20 managed by the user management unit 11.

For example, the setting unit 13 calculates a standard time period for a residual power level of the storage battery 20 to be zero based on the residual power level and a power consumption pace thereof. For example, by substituting the residual power level and the power consumption pace in an expression of (residual power level)/(power consumption pace) with their units being adjusted, it is possible to calculate the standard time period. Further, the setting unit 13 sets the degree of urgency based on the standard time period. For example, the setting unit 13 sets a higher degree of urgency as the standard time is shorter.

For example, the setting unit 13 retains information (a function, a table, or the like) for setting the degree of urgency based on the standard time period in advance. Details about the information are not particularly limited, but for easy understanding of the information, an example is shown as follows. For example, the information may be information such that "degree of urgency: low" is set in a case where the standard time period is equal to or greater than 5 hours, "degree of urgency: intermediate" is set in a case where the standard time period is equal to or greater 1 hour and smaller than 5 hours, "degree of urgency: high" is set in a case where the standard time period is equal to or greater than 30 minutes and smaller than 1 hour, and "degree of urgency: extra-high" is set in a case where the standard time period is smaller than 30 minutes.

In the case of this exemplary embodiment, the first output unit 14 or the second output unit 16 may output the standard time period set by the setting unit 13, in addition to the degree of urgency and the priority rank. Then, an entity that executes a predetermined measure can recognize a standard of a time limit for executing the predetermined measure with respect to each monitoring target user, and can more specifically recognize the degree of urgency, or the like. Further, the monitoring target user can recognize a standard time period for a residual power level of a storage battery of the user to be zero, and can recognize that the entity that executes the predetermined measure recognizes the standard time period. As a result, it is possible to reduce his or her anxiety during a period of time until the time of a measure.

The setting unit 13 may calculate a predicted waiting time until the predetermined measure is executed for each monitoring target user based on the priority ranks determined by the determination unit 15. The calculation method is not particularly limited, but hereinafter, an example thereof will be described. For example, the setting unit 13 may retain information indicating a necessary time (for example, n minutes) for a predetermined measure per a person in advance. Further, the setting unit 13 may calculate a waiting time for a q-th priority ranked monitoring target user using an expression of (q−m)×n−p at a timing when p minutes elapses after the measure for an m-th priority ranked monitoring target user is started. In addition, the setting unit 13 may compare in length the predicted waiting time with the standard time period for each monitoring target user.

The "n" described above may be a time in consideration of a traveling time of the entity that executes the predetermined measure. However, the "n" may be a concept that does not include the traveling time of the entity that executes the predetermined measure, and may be a time necessary for a measure to be actually performed after the entity arrives at the site. In this case, the setting unit 13 may separately calculate a traveling time α(h) of the entity that executes the predetermined measure, and may calculate a waiting time in consideration of α. For example, the setting unit 13 may calculate an average distance Dave (km) between the location of the entity that executes the predetermined measure and the address of each of plural monitoring target users (or the installation position of each of the storage batteries 20), and then, calculate a value obtained by dividing the average distance by a general velocity V (for example, 40 km/h in the case of a car) of traveling means of the entity as α. Further, for example, the setting unit 13 may convert the unit of α into minutes (60α) to calculate a waiting time for a monitoring target user in the q-th priority rank based on an expression of $$(q-m) \times (n+60\alpha) - p.$$

Alternatively, the setting unit 13 may calculate a sum Damo (km) of distances between respective addresses (or respective installation positions of the storage batteries 20) of monitoring target users with priority ranks from the (m+1)-th to the q-th and the location of the entity that executes the predetermined measure, and calculate a value obtained by dividing the sum by a general velocity V (for example, 40 km/h in the case of a car) of traveling means of the entity as α(h). Further, for example, the setting unit 13 may convert the unit of α into minutes (60α) to calculate a waiting time for the q-th priority ranked monitoring target user based on an expression of (q−m)×n−p+60α.

In this case, the first output unit 14 or the second output unit 16 may further output the predicted waiting time until the predetermined measure is executed calculated by the setting unit 13. Further, in a case where the predicted waiting time is longer than the standard time period based on the result of the comparison in length for each monitoring target user, the first output unit 14 or the second output unit 16 may output a warning. Thereby, the entity that executes the predetermined measure can recognize whether the measures by the entity are running slightly late, for example, by comparing the standard time period with the predicted waiting time. In addition, the entity can instantaneously recognize whether the measures by the entity are running slightly late by browsing the warning. Further, the monitoring target user can recognize a processing state of the measure by the entity that executes the predetermined measure. Thus, the monitoring target user can determine whether assistance arrives at the place of the user before power of the storage battery is used up. Thus, it is possible to perform a measure such as "wait for assistance", "ensure power for oneself", or the like, based on the determination result.

An example of a processing flow of the monitoring apparatus 10 of this exemplary embodiment is the same as in the first and second exemplary embodiments.

According to the above-described exemplary embodiment, it is possible to realize the same effects as in the first and second exemplary embodiments. Further, since the degree of urgency can be set based not only on a residual power level of the storage battery but also a power consumption pace thereof, it is possible to improve the accuracy of the degree of urgency to be set.

Fourth Exemplary Embodiment

A monitoring apparatus 10 of this exemplary embodiment is different from the first to third exemplary embodiments in that an installation position of the storage battery 20 is further managed and the degree of urgency is set in consideration of the installation position.

Functional blocks of the monitoring apparatus 10 of this exemplary embodiment are the same as in the first to third exemplary embodiments. Since configurations of the detection unit 12, the first output unit 14, and the second output unit 16 are the same as those of the first to third exemplary embodiments, description thereof will not be repeated. Hereinafter, configurations of the user management unit 11, the setting unit 13, and the determination unit 15 will be described.

The fourth exemplary embodiment is different from the first to third exemplary embodiments in that the user management unit 11 further manages respective installation positions of the storage batteries 20 in addition to residual power levels of the storage batteries 20. The user management unit 11 may further manage a usage state of each of the storage batteries 20, as described in the third exemplary embodiment. FIG. 13 schematically shows an example of information managed by the user management unit 11. Storage battery IDs and installation positions are associated with each other in the information. The installation positions may be indicated by addresses, or other measures such as latitudes and longitudes. The installation positions are registered in the user management unit 11 in advance according to a user's operation.

The fourth exemplary embodiment is different from the first to third exemplary embodiments in that the setting unit 13 sets the degree of urgency based on a distance between a predetermined reference position and an installation position of each storage battery 20 in addition to a residual power level (see FIG. 6) of the storage battery 20 managed by the user management unit 11. The setting unit 13 may set the degree of urgency based on a usage state (see FIG. 12) described in the third exemplary embodiment.

The reference position is registered in the setting unit 13 in advance. The reference position is a place where an entity that performs a predetermined measure is located, for example. That is, the entity prepares for occurrence of a predetermined event at the place. Further, when the predetermined event occurs, the entity departs from the place toward a place where a predetermined monitoring target user is located.

The setting unit 13 calculates the distance between the predetermined reference position and the installation position of each storage battery 20. Since the reference position and the installation position of each storage battery 20 are fixed before a predetermined event occurs, the setting unit 13 may calculate the distance in advance, and the user management unit 11 may manage the information. FIG. 14 schematically shows an example of information calculated and set by the setting unit 13 and managed by the user management unit 11. In the information, storage battery IDs, installation positions of the storage batteries 20, and distances between installation positions of the storage batteries 20 and the reference position are associated with each other.

Figure 15:
FIG. 15 is a diagram schematically showing an example of plural reference positions which are registered in advance in a setting unit 13 of an exemplary embodiment.

Plural reference positions may be present. Thus, as shown in FIG. 15, plural reference positions may be registered in the setting unit 13. In this case, the setting unit 13 may calculate a distance between an installation position of each storage battery 20 and a reference position which is closest to the installation position. Further, the degree of urgency may be set based on the distance.

As the distance between the reference position and the installation position of each storage battery 20 is longer, the setting unit 13 sets a higher degree of urgency.

As a modification example of this exemplary embodiment, the setting unit 13 may set the degree of urgency without using the distance between the reference position and the installation position of each storage battery 20 (for example, the first to third exemplary embodiments), and the determination unit 15 may determine a priority rank based on the distance between the reference position and the storage battery 20 and the set degree of urgency.

For example, in a case where there are plural monitoring target users having the same degree of urgency, the determination unit 15 may assign a higher-priority rank as the distance between the reference position and the storage battery 20 is longer.

An example of a processing flow of the monitoring apparatus 10 of this exemplary embodiment is the same as in the first to third exemplary embodiments.

According to the above-described exemplary embodiment, it is possible to realize the same effects as in the first to third exemplary embodiments. Further, since the degree of urgency can be set based on not only a residual power level of the storage battery but also a distance between a reference position and an installation position of the storage battery 20, it is possible to improve the accuracy of the degree of urgency to be set. Further, since a priority rank can be assigned based on not only the degree of urgency but also the distance between the reference position and the installation position of the storage battery 20 but also, it is possible to appropriately assign the priority rank.

Fifth Exemplary Embodiment

This exemplary embodiment is different from the first to fourth exemplary embodiments in that when a predetermined event (for example, a power failure) is detected, a monitoring target user who needs a predetermined measure is extracted from plural monitoring target users that are registered, and the degree of urgency is set and a priority rank is determined with respect to the extracted monitoring target user, for example.

The range that is affected by a predetermined event is limited. Further, there may be a user who does not use a storage battery when a predetermined event occurs due to being out of the home or the like. Thus, monitoring target users who need a predetermined measure when the predetermined event occurs may be a part of registered monitoring target users.

In this exemplary embodiment, when a predetermined event occurs, monitoring target users who need a predetermined measure are narrowed down. Further, setting of the degree of urgency, determination of a priority rank, and the like are performed with respect to only the narrowed down monitoring target users. Thus, it is possible to increase a processing speed. In addition, it is possible to reduce occurrence of such an inconvenience that an entity that executes a predetermined measure rushes to a monitoring target user who does not need the measure.

Figure 16:
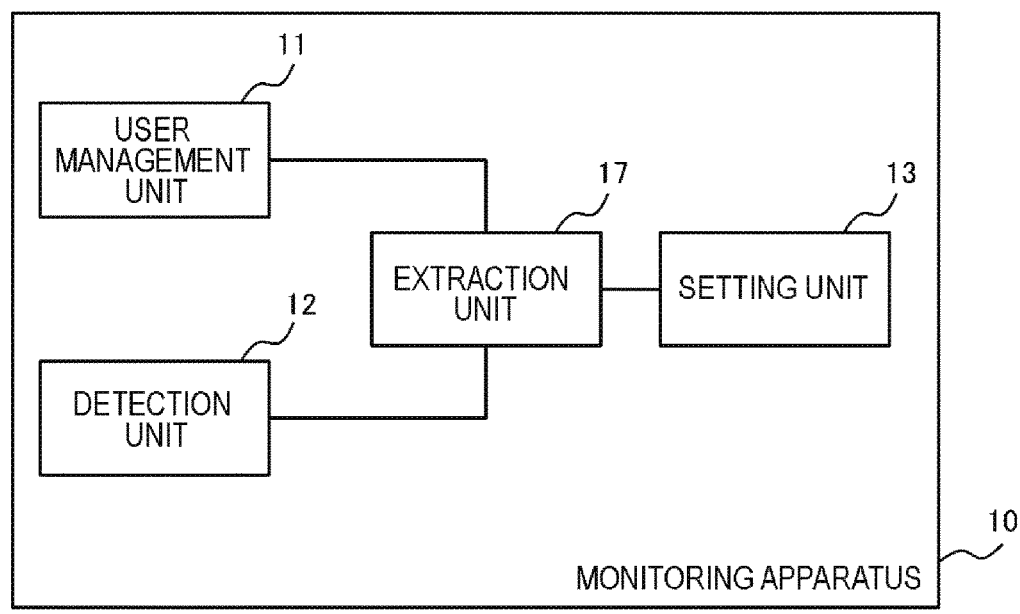
FIG. 16 is a diagram showing an example of functional blocks of a monitoring apparatus of an exemplary embodiment.

FIG. 16 shows an example of functional blocks of this exemplary embodiment. As shown in the figure, the monitoring apparatus 10 of this exemplary embodiment includes a user management unit 11, a detection unit 12, a setting unit 13, and an extraction unit 17. Further, the monitoring apparatus 10 may further include at least a part of a first output unit 14, a determination unit 15, and a second output unit 16. Since configurations of the detection unit 12, the first output unit 14, the determination unit 15, and the second output unit 16 are the same as in the first to fourth exemplary embodiments, description thereof will not be repeated.

If a predetermined event is detected by the detection unit 12, the extraction unit 17 extracts a monitoring target user who needs a predetermined measure from plural monitoring target users registered in the monitoring apparatus 10 in advance. Hereinafter, an example of an extraction process will be described.

For example, as described in the third exemplary embodiment, in a case where the user management unit 11 manages respective usage states of storage batteries 20 (see FIG. 12), if a predetermined event is detected by the detection unit 12, the extraction unit 17 extracts a storage battery 20 (a storage battery 20 of which a power consumption pace is not zero) that is consuming power at that point in time based on the usage state. Further, the extraction unit 17 extracts a monitoring target user corresponding to the extracted storage battery 20 as a monitoring target user who needs a predetermined measure.

As another example, as described in the fourth exemplary embodiment, in a case where the user management unit 11 manages respective installation positions of the storage batteries 20 (see FIG. 13), if the predetermined event is detected by the detection unit 12, the extraction unit 17 further acquires information indicating an area that is affected by the predetermined event.

For example, the extraction unit 17 may receive an input of information indicating the area from an operator who operates the monitoring apparatus 10. Alternatively, information indicating the area that is affected by an event may be input to the monitoring apparatus 10 from an apparatus used by an organization that manages power supply (for example, a power supplier, a person who manages power supply, or the like) through the network 40 when the event occurring. Further, the extraction unit 17 may acquire the information.

In addition, in a case where the monitoring apparatus 10 and the storage battery 20 are configured to communicate with each other even after a predetermined event occurs and the monitoring apparatus 10 is configured to acquire information indicating the occurrence of the predetermined event from the storage battery 20, the extraction unit 17 may acquire information for identifying the storage battery 20 that transmits the information indicating the occurrence of the event. Further, the extraction unit 17 may acquire an installation position (managed by the user management unit 11) of the storage battery 20 as an area that is affected by an event.

Further, if the information indicating the area that is affected the predetermined event is acquired, the extraction unit 17 extracts a storage battery 20 of which the installation position is included in the area, and extracts a monitoring target user corresponding to the storage battery 20 as a monitoring target user who needs a predetermined measure.

The fifth exemplary embodiment is different from the first to fourth exemplary embodiment in that the setting unit 13 sets the degree of urgency by using only the monitoring target user extracted by the extraction unit 17 as a processing target.

Figure 17:
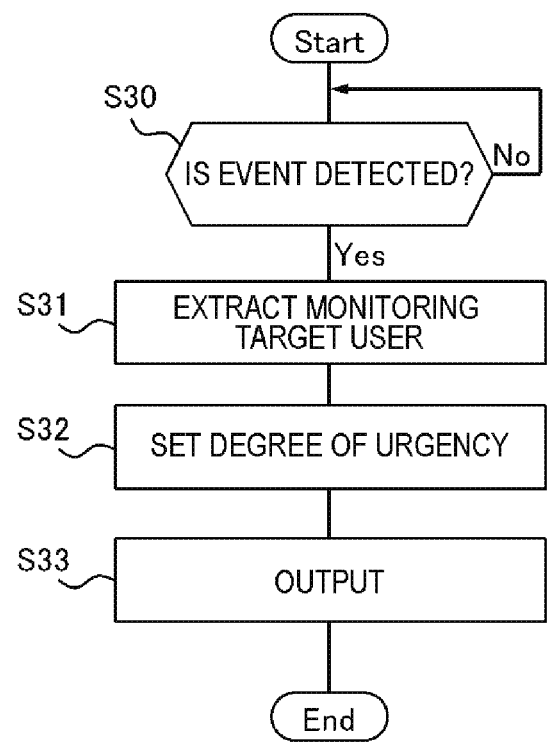
FIG. 17 is a flowchart showing an example of a processing flow of a monitoring apparatus of an exemplary embodiment.

Next, an example of a processing flow of the monitoring apparatus 10 of this exemplary embodiment will be described using a flowchart of FIG. 17.

The detection unit 12 monitors whether a predetermined event occurs (S30). The detection unit 12 continuously monitors until the predetermined event occurs (No in S30).

If the detection unit 12 detects the predetermined event (Yes in S30), the extraction unit 17 extracts a monitoring target user who needs a predetermined measure (S31). Further, the setting unit 13 sets the degree of urgency of need for the predetermined measure with respect to the monitoring target user extracted in S31 as a target (S32). Then, the first output unit 14 outputs the degree of urgency set in S32 (S33).

According to the above-described exemplary embodiment, it is possible to realize the same effect as in the first to fourth exemplary embodiments. Further, when a predetermined event occurs, since setting of the degree of urgency, determination of a priority rank, and the like are performed using only a monitoring target user who truly needs a predetermined measure as a target, it is possible to increase a processing speed.

Further, in the case of this exemplary embodiment, it is possible to exclude a monitoring target user who does not need a predetermined measure from information to be output by the monitoring apparatus 10 toward an entity who performs the predetermined measure. As a result, it is possible to reduce occurrence of such an inconvenience that an entity that executes a predetermined measure based on the degree of urgency and a priority rank output by the monitoring apparatus 10 rushes to a monitoring target user who does not need the measure.

In the first to fifth exemplary embodiments, an example in which the monitoring apparatus 10 acquires information indicating a residual power level of the storage battery 20 or a usage state (a power consumption pace, or the like) thereof from the storage battery 20 is used. The "collection of information from the storage battery 20" may be replaced with "collection of information from another apparatus". For example, in a case where there is an apparatus (for example, an HEMS) that monitors a system power source, a storage battery 20, and a home appliance, and collects and manages data such as consumed power or a residual power level with respect to a monitoring target user, the monitoring apparatus 10 may collect the information from such an apparatus.

Hereinbefore, in the first to fifth exemplary embodiments, a case where the electrical device 30 is a medical device has been described as an example. However, the electrical device 30 may be other devices that need to be continuously operated and are configured to be supplied with power from the storage battery 20. For example, the electrical device 30 may be a communication base station, a data center, or the like. In a case where the electrical device 30 is such a device, it is similarly possible to realize the same effects with the same configuration as in the first to fifth exemplary embodiments.

Hereinafter, examples of reference exemplary embodiments will be described.

1. A monitoring apparatus including:

a user management unit that acquires, in association with each of plural users, a residual power level of a storage battery used by each user;

a detection unit that detects a predetermined event; and a setting unit that sets, when the predetermined event is detected, a degree of urgency of need for a predetermined measure for each user.

2. The monitoring apparatus according to 1, further including:
a determination unit that determines priority ranks for performing predetermined measures with respect to the plural users based on the degree of urgency for each user.

3. The monitoring apparatus according to 1 or 2,
wherein the setting unit sets a higher degree of urgency as the residual power level of the storage battery is lower.

4. The monitoring apparatus according to any one of 1 to 3,
wherein the user management unit further acquires a usage state of each storage battery, and
wherein the setting unit sets the degree of urgency also based on the usage state.

5. The monitoring apparatus according to 4,
wherein the user management unit acquires a power consumption pace as the usage state, and
wherein the setting unit sets the degree of urgency based on a standard time period for a residual power level of the storage battery to be zero, the standard time period being calculated based on the residual power level and the power consumption pace.

6. The monitoring apparatus according to any one of 1 to 5,
wherein the user management unit further acquires an installation position of each storage battery, and
wherein the setting unit sets the degree of urgency also based on a distance between a predetermined reference position and the installation position of each storage battery.

7. The monitoring apparatus according to 6,
wherein the setting unit sets a higher degree of urgency as the distance is longer.

8. The monitoring apparatus according to 6 or 7,
wherein the setting unit sets the degree of urgency for each user based on a distance between the installation position of the storage battery and a reference position closest thereto among plural predetermined reference positions retained by the setting unit.

9. The monitoring apparatus according to any one of 1 to 8, further including:
an extraction unit that extracts, when the predetermined event is detected, a user who needs the predetermined measure from the plural users,
wherein the setting unit sets the degree of urgency of the user extracted by the extraction unit.

10. The monitoring apparatus according to 9,
wherein the user management unit further acquires a usage state of each storage battery, and
wherein the extraction unit extracts, when the predetermined event is detected, a user corresponding to a storage battery that is consuming power at that point in time as the user who needs the predetermined measure.

11. The monitoring apparatus according to 9 or 10,
wherein the user management unit further acquires an installation position of each storage battery, and
wherein the extraction unit acquires, when the predetermined event is detected, information indicating an area that is affected by the predetermined event, and extracts a user corresponding to a storage battery of which an installation position is included in the area as the user who needs the predetermined measure.

12. A program that causes a computer to function as:
a user management unit that acquires, in association with each of plural users, a residual power level of a storage battery used by each user;
a detection unit that detects a predetermined event; and
a setting unit that sets, when the predetermined event is detected, a degree of urgency of need for a predetermined measure for each user based on the residual power level of the storage battery.

12-2. The program according to 12, causing the computer to further function as:
a determination unit that determines priority ranks for performing predetermined measures with respect to the plural users based on the degree of urgency for each user.

12-3. The program according to 12 or 12-2,
wherein the setting unit is caused to set a higher degree of urgency as the residual power level of the storage battery is lower.

12-4. The program according to any one of 12 to 12-3,
wherein the user management unit is caused to further acquire a usage state of each storage battery, and
wherein the setting unit is caused to set the degree of urgency also based on the usage state.

12-5. The program according to 12-4,
wherein the user management unit is caused to acquire a power consumption pace as the usage state, and
wherein the setting unit is caused to set the degree of urgency based on a standard time period for a residual power level of the storage battery to be zero, the standard time period being calculated based on the residual power level and the power consumption pace.

12-6. The program according to any one of 12 to 12-5,
wherein the user management unit is caused to further acquire an installation position of each storage battery, and
wherein the setting unit is caused to set the degree of urgency also based on a distance between a predetermined reference position and the installation position of each storage battery.

12-7. The program according to 12-6,
wherein the setting unit is caused to set a higher degree of urgency as the distance is longer.

12-8. The program according to 12-6 or 12-7,
wherein the setting unit is caused to set the degree of urgency for each user based on a distance between the installation position of the storage battery and a reference position closest thereto among plural predetermined reference positions retained by the setting unit.

12-9. The program according to any one of 12 to 12-8, further causing the computer to function as:
an extraction unit that extracts, when the predetermined event is detected, a user who needs the predetermined measure from the plural users,
wherein the setting unit is caused to set the degree of urgency of the user extracted by the extraction unit.

12-10. The program according to 12-9,
wherein the user management unit is caused to further acquire a usage state of each storage battery, and
wherein the extraction unit is caused to extract, when the predetermined event is detected, a user corresponding to a storage battery that is consuming power at that point in time as the user who needs the predetermined measure.

12-11. The program according to 12-9 or 12-10,
wherein the user management unit is caused to further acquire an installation position of each storage battery, and
wherein the extraction unit is caused to acquire, when the predetermined event is detected, information indicating an area that is affected by the predetermined event, and to extract a user corresponding to a storage battery of which an installation position is included in the area as the user who needs the predetermined measure.

13. A monitoring method executed by a computer, the method including:
    a user management step of acquiring, in association with each of plural users, a residual power level of a storage battery used by each user;
    a detection step of detecting a predetermined event; and
    a setting step of setting, when the predetermined event is detected, a degree of urgency of need for a predetermined measure for each user.

13-2. The monitoring method according to 13, further including:
    a determination step of determining priority ranks for performing predetermined measures with respect to the plural users based on the degree of urgency for each user.

13-3. The monitoring method according to 13 or 13-2,
    wherein in the setting step, a higher degree of urgency is set as the residual power level of the storage battery is lower.

13-4. The monitoring method according to any one of 13 to 13-3,
    wherein in the user management step, a usage state of each storage battery is further acquired, and
    wherein in the setting step, the degree of urgency is set also based on the usage state.

13-5. The monitoring method according to 13-4,
    wherein in the user management step, a power consumption pace is acquired as the usage state, and
    wherein in the setting step, the degree of urgency is set based on a standard time period for a residual power level of the storage battery to be zero, the standard time period being calculated based on the residual power level and the power consumption pace.

13-6. The monitoring method according to any one of 13 to 13-5,
    wherein in the user management step, an installation position of each storage battery is further acquired, and
    wherein in the setting step, the degree of urgency is set also based on a distance between a predetermined reference position and the installation position of each storage battery.

13-7. The monitoring method according to 13-6,
    wherein in the setting step, a higher degree of urgency is set as the distance is longer.

13-8. The monitoring method according to 13-6 or 13-7,
    wherein in the setting step, the degree of urgency for each user is set, using plural predetermined reference positions, based on a distance between the installation position of the storage battery and a reference position closest thereto.

13-9. The monitoring method according to any one of 13 to 13-8, further including:
    an extraction step of extracting, when the predetermined event is detected, a user who needs the predetermined measure from the plural users,
    wherein in the setting step, the degree of urgency of the user extracted by the extraction unit is set.

13-10. The monitoring method according to 13-9,
    wherein in the user management step, a usage state of each storage battery is further acquired, and
    wherein in the extraction step, when the predetermined event is detected, a user corresponding to a storage battery that is consuming power at that point in time is extracted as the user who needs the predetermined measure.

13-11. The monitoring method according to 13-9 or 13-10,
    wherein in the user management step, an installation position of each storage battery is further acquired, and
    wherein in the extraction step, when the predetermined event is detected, information indicating an area that is affected by the predetermined event is acquired, and a user corresponding to a storage battery of which an installation position is included in the area is extracted as the user who needs the predetermined measure.

14. A monitoring system including:
    a monitoring apparatus that includes a user management unit that acquires, in association with each of plural users, a residual power level of a storage battery used by each user, a detection unit that detects a predetermined event, and a setting unit that sets, when the predetermined event is detected, the degree of urgency of need for a predetermined measure for each user; and
    the storage battery that notifies the monitoring apparatus of the residual power level.

This application claims priority based on Japanese Patent Application No. 2014-127428, filed on Jun. 20, 2014, the entire content of which is incorporated herein by reference.

The invention claimed is:

1. A monitoring apparatus, comprising:
    a memory storing computer-executable instructions; and
    at least one processor configured to execute the computer-executable instructions to implement:
    a user management unit configured to acquire, in association with each of a plurality of users, a residual power level of a storage battery used by each user;
    a detection unit configured to detect a predetermined event; and
    a setting unit configured to set, when the predetermined event is detected, a degree of urgency of need for a predetermined measure for each user based on the residual power level of the storage battery.

2. The monitoring apparatus according to claim 1, wherein the at least one processor is further configured to implement:
    a determination unit configured to determine priority ranks for performing predetermined measures with respect to the plurality of users based on the degree of urgency for each user.

3. The monitoring apparatus according to claim 1,
    wherein the setting unit is configured to set the degree of urgency higher as the residual power level of the storage battery is lower.

4. The monitoring apparatus according to claim 1,
    wherein the user management unit is further configured to acquire a usage state of each storage battery, and
    wherein the setting unit is configured to set the degree of urgency based at least in part on the usage state.

5. The monitoring apparatus according to claim 4,
    wherein the user management unit is configured to acquire a power consumption pace as the usage state, and
    wherein the setting unit is configured to set the degree of urgency based on a standard time period for the residual power level of the storage battery to be zero, the standard time period being calculated based on the residual power level and the power consumption pace.

6. The monitoring apparatus according to claim 1,
    wherein the user management unit is further configured to acquire an installation position of each storage battery, and
    wherein the setting unit is configured to set the degree of urgency based at least in part on a distance between a predetermined reference position and the installation position of each storage battery.

7. The monitoring apparatus according to claim 6,
    wherein the setting unit is configured to set the degree of urgency higher as the distance is longer.

8. The monitoring apparatus according to claim 6, wherein the setting unit is configured to set the degree of urgency for each user based on a distance between the installation position of the storage battery and the reference position closest thereto among a plurality of predetermined reference positions retained by the setting unit.

9. The monitoring apparatus according to claim 1, wherein the at least one processor is further configured to implement:
   an extraction unit configured to extract, when the predetermined event is detected, the user who needs the predetermined measure from the plurality of users,
   wherein the setting unit is configured to set the degree of urgency of the user extracted by the extraction unit.

10. The monitoring apparatus according to claim 9, wherein the user management unit is further configured to acquire a usage state of each storage battery, and
   wherein the extraction unit is configured to extract, when the predetermined event is detected, the user corresponding to the storage battery that is consuming power at that point in time as the user who needs the predetermined measure.

11. The monitoring apparatus according to claim 9, wherein the user management unit is further configured to acquire an installation position of each storage battery, and
   wherein the extraction unit is configured to acquire, when the predetermined event is detected, information indicating an area that is affected by the predetermined event, and to extract the user corresponding to the storage battery of which an installation position is included in the area as the user who needs the predetermined measure.

12. A non-transitory, computer-readable storage medium storing a program that, when executed by a computer causes the computer to function as:
   a user management unit configured to acquire, in association with each of a plurality of users, a residual power level of a storage battery used by each user;
   a detection unit configured to detect a predetermined event; and
   a setting unit configured to set, when the predetermined event is detected, a degree of urgency of need for a predetermined measure for each user based on the residual power level of the storage battery.

13. A monitoring method executed by a computer, comprising:
   acquiring, using at least one processor in the computer, in association with each of a plurality of users, a residual power level of a storage battery used by each user;
   detecting, using the at least one processor, a predetermined event; and
   setting, using the at least one processor, when the predetermined event is detected, the degree of urgency of need for a predetermined measure for each user based on the residual power level of the storage battery.

14. A monitoring system comprising:
   a monitoring apparatus comprising:
      a memory storing computer-executable instructions; and
      at least one processor configured to execute the computer-executable instructions to implement:
         a user management unit configured to acquire, in association with each of a plurality of users, a residual power level of a storage battery used by each user,
         a detection unit configured to detect a predetermined event, and
         a setting unit configured to set, when the predetermined event is detected, the degree of urgency of need for a predetermined measure for each user based on the residual power level of the storage battery; and
   the storage battery that notifies the monitoring apparatus of the residual power level.

* * * * *